US012747476B2

(12) United States Patent
Umbarger et al.

(10) Patent No.: US 12,747,476 B2
(45) Date of Patent: Sep. 29, 2026

(54) METHODS FOR COPY NUMBER DETERMINATION

(71) Applicant: Molecular Loop Corporation, Woburn, MA (US)

(72) Inventors: Mark Umbarger, Brookline, MA (US); Eric D. Boyden, Cambridge, MA (US)

(73) Assignee: Molecular Loop Corporation, Woburn, MA (US)

( * ) Notice: Subject to any disclaimer, the term of this patent is extended or adjusted under 35 U.S.C. 154(b) by 1102 days.

(21) Appl. No.: 17/748,316

(22) Filed: May 19, 2022

(65) Prior Publication Data

US 2022/0316010 A1 Oct. 6, 2022

Related U.S. Application Data

(63) Continuation of application No. 15/029,807, filed as application No. PCT/US2014/061138 on Oct. 17, 2014, now Pat. No. 11,339,435.

(60) Provisional application No. 61/892,856, filed on Oct. 18, 2013.

(51) Int. Cl.

| | |
|---|---|
| ***C12Q 1/68*** | (2018.01) |
| ***C12Q 1/6816*** | (2018.01) |
| ***C12Q 1/6883*** | (2018.01) |
| *C12Q 1/6869* | (2018.01) |

(52) U.S. Cl.

CPC ......... *C12Q 1/6883* (2013.01); *C12Q 1/6816* (2013.01); *C12Q 1/6869* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,988,617 | A | 1/1991 | Landegren et al. |
| 5,060,980 | A | 10/1991 | Johnson et al. |
| 5,210,015 | A | 5/1993 | Gelfand et al. |
| 5,234,809 | A | 8/1993 | Boom et al. |
| 5,242,794 | A | 9/1993 | Whiteley et al. |
| 5,348,853 | A | 9/1994 | Wang et al. |
| 5,434,049 | A | 7/1995 | Okano et al. |
| 5,459,307 | A | 10/1995 | Klotz, Jr. |
| 5,486,686 | A | 1/1996 | Zdybel, Jr. et al. |
| 5,491,224 | A | 2/1996 | Bittner et al. |
| 5,494,810 | A | 2/1996 | Barany et al. |
| 5,567,583 | A | 10/1996 | Wang et al. |
| 5,583,024 | A | 12/1996 | McElroy et al. |
| 5,604,097 | A | 2/1997 | Brenner |
| 5,636,400 | A | 6/1997 | Young |
| 5,674,713 | A | 10/1997 | McElroy et al. |
| 5,695,934 | A | 12/1997 | Brenner |
| 5,700,673 | A | 12/1997 | McElroy et al. |
| 5,701,256 | A | 12/1997 | Marr et al. |
| 5,830,064 | A | 11/1998 | Bradish et al. |
| 5,846,719 | A | 12/1998 | Brenner et al. |
| 5,863,722 | A | 1/1999 | Brenner |
| 5,866,337 | A | 2/1999 | Schon |
| 5,869,252 | A | 2/1999 | Bouma et al. |
| 5,869,717 | A | 2/1999 | Frame et al. |
| 5,871,921 | A | 2/1999 | Landegren et al. |
| 5,888,788 | A | 3/1999 | De Miniac |
| 5,942,391 | A | 8/1999 | Zhang et al. |
| 5,971,921 | A | 10/1999 | Timbel |
| 5,993,611 | A | 11/1999 | Moroney et al. |
| 5,994,056 | A | 11/1999 | Higuchi |
| 6,020,127 | A | 2/2000 | Mackenzie et al. |
| 6,033,854 | A | 3/2000 | Kurnit et al. |
| 6,033,872 | A | 3/2000 | Bergsma et al. |
| 6,100,099 | A | 8/2000 | Gordon et al. |
| 6,138,077 | A | 10/2000 | Brenner |
| 6,150,516 | A | 11/2000 | Brenner et al. |
| 6,171,785 | B1 | 1/2001 | Higuchi |
| 6,172,214 | B1 | 1/2001 | Brenner |
| 6,172,218 | B1 | 1/2001 | Brenner |
| 6,197,508 | B1 | 3/2001 | Stanley |
| 6,197,574 | B1 | 3/2001 | Miyamoto et al. |

(Continued)

FOREIGN PATENT DOCUMENTS

| | | | | |
|---|---|---|---|---|
| CA | 2826748 A1 * | 8/2012 | .......... | C12Q 1/6858 |
| EP | 1 321 477 A1 | 6/2003 | | |

(Continued)

OTHER PUBLICATIONS

O'Roak et al. (Science, 2012, vol. 338, p. 1619-1622; epub Nov. 15, 2012) (Year: 2012).*

Abravaya, 1995, Detection of point mutations with a modified ligase chain reaction (Gap-LCR), Nucleic Acids Research, 23(4): 675-682.

Adey, 2010, Rapid, low-input, low-bias construction of shotgun fragment libraries by high-density in vitro transposition, Genome Biol 11:R119, 17 pages.

Ageno, 1969, The Alkaline denaturation of DNA, Biophys J 9(11):1281-1311.

Agrawal, 1990, Site-specific functionalization of oligodeoxynucleotides for non-radioactive labelling, Tetrahedron Let 31:1543-1546.

(Continued)

*Primary Examiner* — Stephanie K Mummert

(74) *Attorney, Agent, or Firm* — Thomas C. Meyers; Sullivan & Worcester LLP

(57) ABSTRACT

The invention generally relates to a method for determining carrier or disease status with respect to a particular disease or condition. In certain embodiments, methods of the invention involve obtaining a sample including nucleic acid from a subject. The nucleic acid includes a genomic locus that is diagnostic for an autosomal recessive disease. The nucleic acid is captured and isolated from the sample and further sequenced. The method further includes analyzing sequence reads to determine a copy number of the captured nucleic acid and further determine a disease status based upon the copy number.

10 Claims, 2 Drawing Sheets

(56) References Cited

U.S. PATENT DOCUMENTS 6,210,891 B1 4/2001 Nyren et al.
6,223,128 B1 4/2001 Allex et al.
6,235,472 B1 5/2001 Landegren et al.
6,235,475 B1 5/2001 Brenner et al.
6,235,501 B1 5/2001 Gautsch et al.
6,235,502 B1 5/2001 Weissman et al.
6,258,568 B1 7/2001 Nyren
6,274,320 B1 8/2001 Rothberg et al.
6,306,597 B1 10/2001 Macevicz
6,352,828 B1 3/2002 Brenner
6,360,235 B1 3/2002 Tilt et al.
6,361,940 B1 3/2002 Van Ness et al.
6,403,320 B1 6/2002 Read et al.
6,462,254 B1 10/2002 Vernachio et al.
6,489,105 B1 12/2002 Matlashewski et al.
6,558,928 B1 5/2003 Landegren
6,569,920 B1 5/2003 Wen et al.
6,582,938 B1 6/2003 Su et al.
6,585,938 B1 7/2003 Machida et al.
6,613,516 B1 9/2003 Christians et al.
6,714,874 B1 3/2004 Myers et al.
6,716,580 B2 4/2004 Gold et al.
6,719,449 B1 4/2004 Augham, Jr. et al.
6,818,395 B1 11/2004 Quake et al.
6,828,100 B1 12/2004 Ronaghi
6,833,246 B2 12/2004 Balasubramanian
6,858,412 B2 2/2005 Willis et al.
6,911,345 B2 6/2005 Quake et al.
6,913,879 B1 7/2005 Schena
6,927,024 B2 8/2005 Dodge et al.
6,941,317 B1 9/2005 Chamberlin et al.
6,948,843 B2 9/2005 Laugharn, Jr. et al.
7,034,143 B1 4/2006 Preparata et al.
7,041,481 B2 5/2006 Anderson et al.
7,049,077 B2 5/2006 Yang
7,057,026 B2 6/2006 Barnes et al.
7,071,324 B2 7/2006 Preparata et al.
7,074,564 B2 7/2006 Landegren et al.
7,074,586 B1 7/2006 Cheronis et al.
7,115,400 B1 10/2006 Adessi et al.
7,169,560 B2 1/2007 Lapidus et al.
7,211,390 B2 5/2007 Rothberg et al.
7,232,656 B2 6/2007 Balasubramanian et al.
7,244,559 B2 7/2007 Rothberg et al.
RE39,793 E 8/2007 Brenner
7,264,929 B2 9/2007 Rothberg et al.
7,282,337 B1 10/2007 Harris
7,297,518 B2 11/2007 Quake et al.
7,320,860 B2 1/2008 Landegren et al.
7,323,305 B2 1/2008 Leamon et al.
7,335,762 B2 2/2008 Rothberg et al.
7,351,528 B2 4/2008 Landegren
7,393,665 B2 7/2008 Brenner
7,510,829 B2 3/2009 Faham et al.
7,523,117 B2 4/2009 Zhang et al.
7,537,889 B2 5/2009 Sinha et al.
7,537,897 B2 5/2009 Brenner et al.
7,544,473 B2 6/2009 Brenner
7,582,431 B2 9/2009 Drmanac et al.
7,598,035 B2 10/2009 Macevicz
7,629,151 B2 12/2009 Gold et al.
7,642,056 B2 1/2010 Ahn et al.
7,666,593 B2 2/2010 Lapidus
7,700,323 B2 4/2010 Willis et al.
7,774,962 B1 8/2010 Ladd
7,776,616 B2 8/2010 Heath et al.
RE41,780 E 9/2010 Anderson et al.
7,790,388 B2 9/2010 Landegren et al.
7,809,509 B2 10/2010 Milosavljevic
7,822,555 B2 * 10/2010 Huang .................. G16B 25/20
435/6.12
7,835,871 B2 11/2010 Kain et al.
7,862,999 B2 1/2011 Zheng et al.
7,865,534 B2 1/2011 Genstruct
7,883,849 B1 2/2011 Dahl
7,957,913 B2 6/2011 Chinitz et al.
7,960,120 B2 6/2011 Rigatti et al.
7,985,716 B2 7/2011 Yershov et al.
7,993,880 B2 8/2011 Willis et al.
8,024,128 B2 9/2011 Rabinowitz et al.
8,114,027 B2 2/2012 Triva
8,165,821 B2 4/2012 Zhang
8,209,130 B1 6/2012 Kennedy et al.
8,283,116 B1 10/2012 Bhattacharyya et al.
8,462,161 B1 6/2013 Barber
8,463,895 B2 6/2013 Arora et al.
8,474,228 B2 7/2013 Adair et al.
8,496,166 B2 7/2013 Burns et al.
8,529,744 B2 9/2013 Marziali et al.
8,586,309 B2 * 11/2013 Kopan ................. C12Q 1/6813
536/23.1
8,738,300 B2 5/2014 Porreca et al.
8,778,609 B1 7/2014 Umbarger
8,812,422 B2 8/2014 Nizzari et al.
8,847,799 B1 9/2014 Kennedy et al.
8,976,049 B2 3/2015 Kennedy et al.
9,074,244 B2 7/2015 Sparks et al.
9,115,387 B2 8/2015 Umbarger
9,127,312 B2 * 9/2015 Regan .................. C12Q 1/6883
9,228,233 B2 1/2016 Kennedy et al.
9,292,527 B2 3/2016 Kennedy et al.
9,535,920 B2 1/2017 Kennedy et al.
9,567,639 B2 2/2017 Oliphant et al.
9,677,124 B2 6/2017 Umbarger
10,066,259 B2 9/2018 Gore et al.
10,202,637 B2 2/2019 Umbarger
10,227,635 B2 3/2019 Umbarger et al.
10,604,799 B2 3/2020 Porreca et al.
10,683,533 B2 6/2020 Umbarger et al.
10,851,414 B2 12/2020 Boyden et al.
11,339,435 B2 * 5/2022 Umbarger ............ C12Q 1/6816
2001/0007742 A1 7/2001 Landergren
2001/0046673 A1 11/2001 French et al.
2002/0001800 A1 1/2002 Lapidus
2002/0040216 A1 4/2002 Dumont et al.
2002/0042052 A1 4/2002 Nilsen et al.
2002/0091666 A1 7/2002 Rice et al.
2002/0164629 A1 11/2002 Quake et al.
2002/0172954 A1 11/2002 Mao et al.
2002/0182609 A1 12/2002 Arcot
2002/0187496 A1 12/2002 Andersson et al.
2002/0190663 A1 12/2002 Rasmussen
2003/0166057 A1 9/2003 Hildebrand et al.
2003/0175709 A1 9/2003 Murphy et al.
2003/0177105 A1 9/2003 Xiao et al.
2003/0203370 A1 10/2003 Yakhini et al.
2003/0208454 A1 11/2003 Rienhoff et al.
2003/0224384 A1 12/2003 Sayood et al.
2004/0029264 A1 2/2004 Robbins
2004/0053275 A1 3/2004 Shafer
2004/0106112 A1 6/2004 Nilsson et al.
2004/0121373 A1 6/2004 Friedlander et al.
2004/0142325 A1 7/2004 Mintz et al.
2004/0152108 A1 8/2004 Keith et al.
2004/0161773 A1 8/2004 Rogan et al.
2004/0170965 A1 9/2004 Scholl et al.
2004/0171051 A1 9/2004 Holloway
2004/0175719 A1 9/2004 Christians
2004/0197813 A1 10/2004 Hoffman et al.
2004/0209299 A1 10/2004 Pinter et al.
2005/0003369 A1 1/2005 Christians et al.
2005/0026204 A1 2/2005 Landegren
2005/0032095 A1 2/2005 Wigler et al.
2005/0048505 A1 3/2005 Fredrick et al.
2005/0059048 A1 3/2005 Gunderson et al.
2005/0100900 A1 5/2005 Kawashima et al.
2005/0112590 A1 5/2005 Boom et al.
2005/0186589 A1 8/2005 Kowalik et al.
2005/0214811 A1 9/2005 Margulies et al.
2005/0244879 A1 11/2005 Schumm et al.
2005/0250147 A1 11/2005 Macevicz
2005/0272065 A1 12/2005 Lakey et al.
2006/0008824 A1 1/2006 Ronaghi et al.
2006/0019304 A1 1/2006 Hardenbol et al.

(56) References Cited

U.S. PATENT DOCUMENTS

2006/0024681 A1 2/2006 Smith et al.
2006/0030536 A1 2/2006 Yu et al.
2006/0078894 A1 4/2006 Winkler et al.
2006/0149047 A1 7/2006 Nanduri et al.
2006/0177837 A1 8/2006 Borozan et al.
2006/0183132 A1 8/2006 Fu et al.
2006/0192047 A1 8/2006 Goossen
2006/0195269 A1 8/2006 Yeatman et al.
2006/0246500 A1 11/2006 Browne
2006/0263789 A1 11/2006 Kincaid
2006/0281098 A1 12/2006 Miao et al.
2006/0286577 A1 12/2006 Jia
2006/0292585 A1 12/2006 Nautiyal et al.
2006/0292611 A1 12/2006 Berka et al.
2007/0009925 A1 1/2007 Fang et al.
2007/0020640 A1 1/2007 McCloskey et al.
2007/0042369 A1 2/2007 Reese et al.
2007/0092883 A1 4/2007 Schouten et al.
2007/0114362 A1 5/2007 Feng et al.
2007/0128624 A1 6/2007 Gormley et al.
2007/0161013 A1 7/2007 Hantash
2007/0162983 A1 7/2007 Hesterkamp et al.
2007/0166705 A1 7/2007 Milton et al.
2007/0212704 A1 9/2007 Dong et al.
2007/0225487 A1 9/2007 Nilsson et al.
2007/0238122 A1 10/2007 Allbritton et al.
2007/0244675 A1 10/2007 Shai et al.
2007/0264653 A1 11/2007 Berlin et al.
2007/0292408 A1 12/2007 Singh et al.
2008/0003142 A1 1/2008 Link et al.
2008/0014589 A1 1/2008 Link et al.
2008/0076118 A1 3/2008 Tooke et al.
2008/0081330 A1 4/2008 Kahvejian
2008/0085836 A1 4/2008 Kearns et al.
2008/0090239 A1 4/2008 Shoemaker et al.
2008/0125324 A1 5/2008 Petersdorf et al.
2008/0176209 A1 7/2008 Muller et al.
2008/0269068 A1 10/2008 Church et al.
2008/0280955 A1 11/2008 McCamish
2008/0293589 A1 11/2008 Shapero
2009/0009904 A1 1/2009 Yasuna et al.
2009/0019156 A1 1/2009 Mo et al.
2009/0026082 A1 1/2009 Rothberg et al.
2009/0029385 A1 1/2009 Christians et al.
2009/0035777 A1 2/2009 Kokoris et al.
2009/0042206 A1 2/2009 Schneider et al.
2009/0098551 A1 4/2009 Landers et al.
2009/0099041 A1 4/2009 Church et al.
2009/0105081 A1 4/2009 Rodesch et al.
2009/0119313 A1 5/2009 Pearce
2009/0127589 A1 5/2009 Rothberg et al.
2009/0129647 A1 5/2009 Dimitrova et al.
2009/0156412 A1 6/2009 Boyce, IV et al.
2009/0163366 A1 6/2009 Nickerson et al.
2009/0181389 A1 7/2009 Li et al.
2009/0191565 A1 7/2009 Lapidus et al.
2009/0192047 A1 7/2009 Parr et al.
2009/0202984 A1 8/2009 Cantor
2009/0203014 A1 8/2009 Wu et al.
2009/0220955 A1 9/2009 Verrant
2009/0226975 A1 9/2009 Sabot et al.
2009/0233814 A1 9/2009 Bashkirov et al.
2009/0298064 A1 12/2009 Batzoglou et al.
2009/0301382 A1 12/2009 Patel
2009/0318310 A1 12/2009 Liu et al.
2010/0035243 A1 2/2010 Muller et al.
2010/0035252 A1 2/2010 Rothberg et al.
2010/0063742 A1 3/2010 Hart et al.
2010/0069263 A1 3/2010 Shendure et al.
2010/0076185 A1 3/2010 Adey et al.
2010/0086914 A1 4/2010 Bentley et al.
2010/0086926 A1 4/2010 Craig et al.
2010/0105107 A1 4/2010 Hildebrand et al.
2010/0137143 A1 6/2010 Rothberg et al.
2010/0137163 A1 6/2010 Link et al.
2010/0143908 A1 6/2010 Gillevet
2010/0159440 A1 6/2010 Messier et al.
2010/0188073 A1 7/2010 Rothberg et al.
2010/0196911 A1 8/2010 Hoffman et al.
2010/0197507 A1 8/2010 Rothberg et al.
2010/0216151 A1 8/2010 Lapidus et al.
2010/0216153 A1 8/2010 Lapidus et al.
2010/0227329 A1 9/2010 Cuppens
2010/0248984 A1 9/2010 Shaffer et al.
2010/0282617 A1 11/2010 Rothberg et al.
2010/0285578 A1 11/2010 Selden et al.
2010/0297626 A1 11/2010 McKernan et al.
2010/0300559 A1 12/2010 Schultz et al.
2010/0300895 A1 12/2010 Nobile et al.
2010/0301042 A1 12/2010 Kahlert
2010/0301398 A1 12/2010 Rothberg et al.
2010/0304982 A1 12/2010 Hinz et al.
2010/0311061 A1 12/2010 Korlach et al.
2010/0330619 A1 12/2010 Willis et al.
2011/0004413 A1 1/2011 Carnevali et al.
2011/0009278 A1 1/2011 Kain et al.
2011/0015863 A1 1/2011 Pevzner et al.
2011/0021366 A1 1/2011 Chinitz et al.
2011/0034342 A1 2/2011 Fox
2011/0092375 A1 4/2011 Zamore et al.
2011/0098193 A1 4/2011 Kingsmore et al.
2011/0117544 A1 5/2011 Lexow
2011/0159499 A1* 6/2011 Hindson .............. C12Q 1/6827 435/6.12
2011/0166029 A1 7/2011 Margulies et al.
2011/0224105 A1 9/2011 Kum et al.
2011/0230365 A1 9/2011 Rohlfs et al.
2011/0257889 A1 10/2011 Klammer et al.
2011/0288780 A1 11/2011 Rabinowitz et al.
2011/0301042 A1 12/2011 Steinmann et al.
2012/0015050 A1 1/2012 Abkevich et al.
2012/0021930 A1 1/2012 Schoen et al.
2012/0046877 A1 2/2012 Hyland et al.
2012/0059594 A1 3/2012 Hatchwell et al.
2012/0074925 A1 3/2012 Oliver
2012/0079980 A1 4/2012 Taylor et al.
2012/0115736 A1 5/2012 Bjornson et al.
2012/0164630 A1 6/2012 Porreca et al.
2012/0165202 A1 6/2012 Porreca et al.
2012/0179384 A1 7/2012 Kuramitsu et al.
2012/0214678 A1 8/2012 Rava et al.
2012/0216151 A1 8/2012 Sarkar et al.
2012/0236861 A1 9/2012 Ganeshalingam et al.
2012/0245041 A1 9/2012 Brenner et al.
2012/0252020 A1 10/2012 Shuber
2012/0252684 A1 10/2012 Selifonov et al.
2012/0258461 A1 10/2012 Weisbart
2012/0270212 A1 10/2012 Rabinowitz et al.
2012/0270739 A1 10/2012 Rava et al.
2013/0129755 A1 5/2013 Song
2013/0130921 A1 5/2013 Gao et al.
2013/0178378 A1 7/2013 Hatch et al.
2013/0183672 A1 7/2013 de Laat et al.
2013/0222388 A1 8/2013 McDonald
2013/0268206 A1 10/2013 Porreca et al.
2013/0268474 A1 10/2013 Nizzari et al.
2013/0274146 A1 10/2013 Umbarger et al.
2013/0275103 A1 10/2013 Struble et al.
2013/0288242 A1 10/2013 Stoughton et al.
2013/0323730 A1 12/2013 Curry et al.
2013/0332081 A1 12/2013 Reese et al.
2013/0337447 A1 12/2013 Porreca et al.
2013/0344096 A1 12/2013 Chiang et al.
2014/0129201 A1 5/2014 Kennedy et al.
2014/0136120 A1 5/2014 Colwell et al.
2014/0206552 A1 7/2014 Rabinowitz et al.
2014/0222349 A1 8/2014 Higgins et al.
2014/0228226 A1 8/2014 Yin et al.
2014/0255931 A1 9/2014 Porreca et al.
2014/0274741 A1 9/2014 Hunter et al.
2014/0308667 A1 10/2014 Umbarger
2014/0318274 A1 10/2014 Zimmerman et al.

(56) References Cited

U.S. PATENT DOCUMENTS

| | | | |
|---|---|---|---|
| 2014/0342354 | A1 | 11/2014 | Evans et al. |
| 2014/0361022 | A1 | 12/2014 | Finneran |
| 2015/0051085 | A1 | 2/2015 | Vogelstein et al. |
| 2015/0056613 | A1 | 2/2015 | Kural |
| 2015/0111208 | A1 | 4/2015 | Umbarger et al. |
| 2015/0178445 | A1 | 6/2015 | Cibulskis et al. |
| 2015/0258170 | A1 | 9/2015 | McCabe et al. |
| 2015/0299767 | A1 | 10/2015 | Armour et al. |
| 2015/0310163 | A1 | 10/2015 | Kingsmore et al. |
| 2015/0354003 | A1 | 12/2015 | Umbarger |
| 2016/0003812 | A1 | 1/2016 | Porreca et al. |
| 2016/0034638 | A1 | 2/2016 | Spence et al. |
| 2016/0068889 | A1 | 3/2016 | Gole et al. |
| 2016/0188793 | A1 | 6/2016 | Muzzey et al. |
| 2016/0210486 | A1 | 7/2016 | Porreca et al. |
| 2016/0251719 | A1 | 9/2016 | Umbarger |
| 2017/0044610 | A1 | 2/2017 | Johnson |
| 2017/0129964 | A1 | 5/2017 | Cheung |
| 2017/0183731 | A1 | 6/2017 | Mann et al. |
| 2017/0275676 | A1 | 9/2017 | Umbarger |
| 2018/0371533 | A1 | 12/2018 | Gore et al. |
| 2019/0233881 | A1 | 8/2019 | Umbarger et al. |
| 2020/0181696 | A1 | 6/2020 | Porreca et al. |

FOREIGN PATENT DOCUMENTS

| | | | | |
|---|---|---|---|---|
| EP | 1 564 306 | A2 | 8/2005 | |
| EP | 2425240 | A2 | 3/2012 | |
| EP | 2 437 191 | A2 | 4/2012 | |
| EP | 2716766 | A1 | 4/2014 | |
| WO | 95/011995 | A1 | 5/1995 | |
| WO | 1996/019586 | A1 | 6/1996 | |
| WO | 98/014275 | A1 | 4/1998 | |
| WO | 98/044151 | A1 | 10/1998 | |
| WO | 00/018957 | A1 | 4/2000 | |
| WO | 02/093453 | A2 | 11/2002 | |
| WO | 2004/018497 | A2 | 3/2004 | |
| WO | 2004/083819 | A2 | 9/2004 | |
| WO | 2005/003304 | A2 | 1/2005 | |
| WO | 2006/084132 | A2 | 8/2006 | |
| WO | 2007/010251 | A2 | 1/2007 | |
| WO | 2007/061284 | A1 | 5/2007 | |
| WO | 2007/107717 | A1 | 9/2007 | |
| WO | 2007/123744 | A2 | 11/2007 | |
| WO | 2007/135368 | A2 | 11/2007 | |
| WO | 2008067551 | A2 | 6/2008 | |
| WO | 2009/036525 | A2 | 3/2009 | |
| WO | 2009/076238 | A2 | 6/2009 | |
| WO | 2010/024894 | A1 | 3/2010 | |
| WO | 2010/115154 | A1 | 10/2010 | |
| WO | 2010/126614 | A2 | 11/2010 | |
| WO | 2011/006020 | A1 | 1/2011 | |
| WO | 2011066476 | A1 | 6/2011 | |
| WO | 2011067378 | A1 | 6/2011 | |
| WO | 2011/102998 | A2 | 8/2011 | |
| WO | 2011/155833 | A2 | 12/2011 | |
| WO | 2012/006291 | A2 | 1/2012 | |
| WO | 2012/040387 | A1 | 3/2012 | |
| WO | 2012/051208 | A2 | 4/2012 | |
| WO | 2012/087736 | A1 | 6/2012 | |
| WO | 2012/109500 | A2 | 8/2012 | |
| WO | 2012/134884 | A1 | 10/2012 | |
| WO | 2012/149171 | A1 | 11/2012 | |
| WO | WO-2012170725 | A2 * | 12/2012 | ........... C12Q 1/6883 |
| WO | 2013/058907 | A1 | 4/2013 | |
| WO | 2013/148496 | A1 | 10/2013 | |
| WO | 2013/177086 | A1 | 11/2013 | |
| WO | 2013/191775 | A2 | 12/2013 | |
| WO | 2014/052909 | A2 | 4/2014 | |
| WO | 2014/074246 | A1 | 5/2014 | |
| WO | 2015/119941 | A2 | 8/2015 | |

OTHER PUBLICATIONS

Akhras, 2007, Connector inversion probe technology: A powerful one-primer multiplex DNA amplification system for numerous scientific applications, PLoSOne 2(9):e915.
Akhras, 2007, PathogenMip Assay: a multiplex pathogen detection assay, PLOS One 2:e2230.
Alazard, 2002, Sequencing of production-scale synthetic oligonucleotides by enriching for coupling failures using matrix-assisted laser desorption/ ionization time-of-flight mass spectrometry, Anal Biochem 301:57-64 by enrichment of coupling failures using matrix-assisted laser desorption/Curr Protoc Nucleic Acid Chem, Chapter 10, Unit 10:1-7.
Alazard, 2006, Sequencing oligonucleotides ionization time-of-flight mass spectrometry.
Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Archer, 2014, Selective and flexible depletion of problematic sequences from RNA-seq libraries at the cDNA stage, BMC Genomics 15(1):401, 9 pages.
Ball, 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3(65ra4), 15 pages.
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bhangale, 2006, Automating resequencing-based detection of insertion-deletion polymorphisms, Nature Genetics 38:1457-1462.
Bickle, 1993, Biology of DNA restriction, Microbiol Rev 57(2):434-50.
Blasczyk, 1996, Sequence analysis of the 2nd intron revealed common sequence motifs providing the means for a unique sequencing based typing protocol of the HLA-A locus, Tissue Antigens, 47:102-110.
Bonfield, 2013, Compression of FASTQ and SAM format sequencing data, PLoS One 8(3):e59190, 10 pages.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013, 2 pages.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.

(56) References Cited

OTHER PUBLICATIONS

Brinkman, 2004, Splice Variants as Cancer Biomarkers, Clin Biochem 37:584-594.
Brison, 1982, General method for cloning amplified DNA by differential screening, Mol Cell Biol 2(5):578-587.
Brown, 1979, Chemical synthesis and cloning of a tyrosine tRNA gene, Methods Enzymol, 68:109-51.
Browne, 2002, Metal ion-catalyzed nucleic acid alkylation and fragmentation, J Am Chem Soc 124(27):7950-7962.
Brownstein, 2014, An international effort towards developing standards for best practices in analysis, interpretation and reporting of clinical genome sequencing results in the Clarity Challenge, Genome Biol 15:R53, 8 pages.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA., 24 pages.
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
Chaisson, 2004, Fragment assembly with short reads, Bionormatics, 20:2067-2074.
Challis, 2012, An integrative variant analysis suite for whole exome next-generation sequencing data, BMC Informatics 13(8):1-12.
Chan, 2011, Natural and engineered nicking endonucleases-from cleavage mechanism to engineering of strand-specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013, 2 pages.
Chevreux, 1999, Genome sequence assembly using trace signals and additional sequence information, Proc GCB 99:45-56.
Chirgwin, 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Chou, 2010, DNA Sequence Capture and Enrichment by Microarray Followed by Next-Generation Sequencing for Targeted Resequencing: Neurofibromatosis Type 1 Gene as a Model, Clinical Chemistry, 56(1):62-72.
Ciotti, 2004, Triplet repeat prmied PCR (TP PCR) in molecular diagnostic testing for Friedrich ataxia, J Mol Diag 6(4):285-9.
Cock, 2010, The Sanger FASTQ file format for sequences with quality scores, and the Solexa/Illumina FASTQ variants, Nucleic Acids Res 38(6):1767-1771.
Collins, 2004, Finishing the euchromatic sequence of the human genome, Nature 431(7011):931-45.
Craig, 1997, Removal of repetitive sequences from FISH probes, Hum Genet 100:472.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355-362.
Cronin, 1996, Cystic Fibrosis Mutation Detection by Hybridization to Light-Generated DNA Probe Arrays Human Mutation 7:244-255.
Dahl, 2005, Multiplex amplification enabled by selective circularization of large sets of genomic DNA fragments, Nucleic Acids Res 33(8):e71, 7 pages.
Daly, 2007, Multiplex Assay for Comprehensive Genotyping of Genes Involved in Drug Metabolism, Excretion, and Transport, Clinical Chemistry, 53:7:1222-1230.
Danecek, 2011, The variant call format and VCFtools, Bioinformatics 27(15):2156-2158.
De la Bastide, 2007, Assembling genome DNA sequences with PHRAP, Current Protocols in Bioinformatics 17:11.4.1-11.4.15, 15 pages.
Delcher, 1999, Alignment of whole genomes, Nuc Acids Res 27(11):2369-2376.
Den Dunnen, 2003, Mutation Nomenclature, Curr Prot Hum Genet 7.13.1-7.13.8, 8 pages.
Deng, 2009, targeted bisulfite sequencing reveals changes in DNA methylation, Nat Biotech 27(4):353-360.
Deng, 2012, Supplementary Material, Nature Biotechnology, S1-1-S1-1 1, Retrieved from the Internet on Oct. 24, 2012, 12 pages.
Deorowicz, 2013, Data compression for sequencing data, Alg for Mole Bio 8:25, 13 pages.
Diep, 2012, Library-free methylation sequencing with bisulfite padlock probes, Nature Methods 9:270-272 (and supplemental information).
Diguistini, 2009, De novo sequence assembly of a filamentous fungus using Sanger, 454 and Illumina sequence data, Genome Biology, 10:R94, 12 pages.
Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5):1534-1544.
Dong, 2011, Mutation surveyor: An in silico tool for sequencing analysis, Methods Mol Biol 760:223-37.
Dou, 2012, Reference-free SNP calling: improved accuracy by preventing incorrect calls from repetitive genomic regions, Biology Direct 7:17.
Drmanac, 1992, Sequencing by hybridization: towards an automated sequencing of one million M13 clones arrayed on membranes, Elctrophoresis 13:566-573.
Dudley, 2009, A quick guide for developing effective bioinformatics programming skills, PLoS Comp Biol 5(12):e1000589, 7 pages.
Ericsson, 2008, A dual-tag microarray platform for high-performance nucleic acid and protein analyses, Nucl Acids Res 36:e45, 9 pages.
Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014, 2 pages.
Fitch, 1970, Distinguishing homologs from analogous proteins, Syst Biol 19(2):99-113.
Flaschker, 2007, Description of the mutations in 15 subjects with variant forms of maple syrup urine disease, J Inherit Metab Dis 30:903-909.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60, 28 pages.
Fu, 2010, Repeat subtraction-mediated sequence capture from a complex genome, The Plant Journal, 62:898-909.
Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Giusti, 1993, Synthesis and Characterization of f-Fluorescent-dye-labeled Oligonucleotides, PCR Meth Appl 2:223-227.
Glover, 1995, Sequencing of oligonucleotides using high performance liquid chromatography and electrospray mass spectrometry, Rapid Com Mass Spec 9:897-901.
Gnirke, 2009, Solution hybrid selection with ultra-long oligonucleotides for massively parallel targeted sequencing, nature biotechnology 27:182-9.

(56) References Cited

OTHER PUBLICATIONS

Goto, 1994, A Study on Development of a Deductive Object-Oriented Database and Its Application to Genome Analysis, PhD Thesis, Kyushu University, Kyushu, Japan, 106 pages.
Goto, 2010, BioRuby: bioinformatics software for the Ruby programming language, Bioinformatics, 26(20):2617-2619.
Green, 2005, Suicide polymerase endonuclease restriction, a novel technique for enhancing PCR amplification of minor DNA template, Appl Env Microbiol 71(8):4721-4727.
Guerrero-Fernandez, 2013, FQbin: a compatible and optimize dformat for storing and managing sequence data, WBBIO Proceedings, Granada 337-344.
Gupta, 1991, A general method for the synthesis of 3'-sulfhydryl and phosphate group containing oligonucleotides, Nucl Acids Res 19(11):3019-3025.
Gupta, 2014, Expanding the genetic toolkit: ZFNs, TALENs, and CRISPR-Cas9, J Clin Invest 124(10):4154-4161.
Gustincich, 1991, A fast method for high-quality genomic DNA extraction from whole humna blood, BioTechniques 11(3):298-302.
Gut, 1995, A procedure for selective DNA alkylation and detection by mass spectrometry, Nucl Acids Res 23(8):1367-1373.
Hahnen, 1996, Hybrid Survival Motor Neuron Genes in Patients with Autosomal Recessive Spinal Muscular Atrophy: New Insights into Molecular Mechanisms Responsible for the Disease, Am J Hum Genet, 59:1057-1065.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18(5):821-829.
Zhang, 2011, Is Mitochondrial IRNAphe Variant m.593T.Ca Synergistically Pathogenic Mutation in Chinese LHON Families with m.11778G.A? PLoS ONE 6(10):e26511, 8 pages.
Zhao, 2009, PGA4genomics for comparative genome assembly based on genetic algorithm optimization, Genomics 94(4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30(8):1073-1080.
Zhulidov, 2004, Simple cDNA normalization using kamchatka crab duplex-specific nuclease, Nucl Acids Res 32(3):e37, 8 pages.
Zimmerman, 2010, A novel custom resequencing array for dilated cardiomyopathy, Gen Med 12(5):268-78.
Zimran, 1990, A glucocerebrosidase fusion gene in Gaucher disease, J Clin Invest 85:219-222.
Zuckerman, 1987, Efficient methods for attachment of thiol specific probes to the 3'-ends of synthetic oligodeoxyribonucleotides, Nucl Acid Res 15(13):5305-5321.
O'Roak, 2012, Multiplex targeted sequencing identifies recurrently mutated genes in autism spectrum disorders, Science 338(6114):1619-1622.
Defner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Okou, 2007, Microarray-based genomic selection for high-throughput reseuqencing, Nat Meth 4(11):907-909.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res, 3:2985-2999.
Ostrer, 2001, A genetic profile of contemporary Jewish populations, Nat Rev Genet 2(11):891-8.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130, 27 pages.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.
Pearson, 1988, Improved tools for biological sequence comparison, PNAS 85(8):2444-8.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplificaiton of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013, 2 pages.
Pourmand, 2006, PathgoenMIPer: a tool for the design of molecular inversion probes, BMC informatics 7:500, 10 pages.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed., 72 pages.
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLos ONE 3:e3373, 12 pages.

(56) References Cited

OTHER PUBLICATIONS

Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41.
Rosendahl, 2013, CFTR, SPINK1, CTRC and PRSS1 variants in chronic pancreatitis: is the role of mutated CFTR overestimated?, Gut 62:582-592.
Rothberg, 2011, An integrated semiconductor device enabling non-optical genome sequencing. Nature 475, 348-352.
Rowntree, 2003, The phenotypic consequences of CFTR mutations, Ann Hum Gen 67:471-485.
Saihan, 2009, Update on Usher syndrome, Curr Op Neurology 22(1):19-24.
Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1987, Isolation of differentially expressed genes, Meth Enzym 152:423-432.
Sauro, 2004, How Do You Calculate a Z-Score/ Sigma Level?, https://www.measuringusability.com/zcalc.htm (online publication), 3 pages.
Sauro, 2004, What's a Z-score and Why Use It in Usability Testing?, https://www.measuringusability.com/z.htm (online publication), 4 pages.
Schadt, 2010, A window into third-generation sequencing, Human Mol Genet 19(R2):R227-40.
Schatz, 2010, Assembly of large genomes using second-generation sequencing, Genome Res., 20:1165-1173.
Schiffman, 2007, Adapting molecular inversion probe (MIP) technology for allele quantification in childhood leukemia, Journal of Clinical Oncology, 25, p530, 5 pages.
Schiffman, 2009, Molecular inversion probes reveal patterns of 9p21 deletion and copy number aberrations in childhood leukemia, Cancer Genetics and Cytogenetics 193:9-18.
Schneeberger, 2011, Reference-guided assembly of four diverse *Arabidopsis thaliana* genomes, PNAS 108(25):10249-10254.
Schouten, 2002, Relative Quantification of 40 Nucleic Acid Sequences by Multiplex Ligation-Dependent Probe Amplification, Nucle Acids Res 30 (12):257, 13 pages.
Schrijver, 2005, Diagnostic testing by CFTR gene mutation analysis in a large group of Hispanics, J Mol Diag 7(2):289-299.
Schuette, 1995, Sequence analysis of phosphorothioate oligonucleotides via matrix-assisted laser desorption ionization time-of-flight mass spectrometry, J Pharm Biomed Anal 13:1195-1203.
Schwartz, 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shagin, 2002, A novel method for SNP detection, Genome Res 12:1935-1942.
Shen, 2011, High quality DNA sequence capture of 524 disease candidate genes, PNAS 108(16):6549-6554.
Harris, 2006, Defects can increase the melting temperature of DNA-nanoparticle assemblies, J Phys Chem B 110(33):16393-6.
Harris, 2008, Helicos True Single Molecule Sequencing (tSMS) Science 320:106-109.
Harris, 2008, Single-molecule DNA sequencing of a viral genome, Science 320(5872):106-9.
Heger, 2006, Protonation of Cresol Red in Acidic Aqueous Solutions Caused by Freezing, J Phys Chem B 110(3):1277-1287.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hodges, 2007, Genome-wide in situ exon capture for selective resequencing, Nat Genet 39(12):1522-7.
Holland, 2008, BioJava: an open-source framework for bioinformatics, Bioinformatics 24(18):2096-2097.
Homer, 2008, Resolving Individuals Contributing Trace Amounts of DNA to Highly Complex Mixtures Using High-Density SNP Genotyping Microarrays. PLoS ONE 4(8):e1000167, 9 pages.
Homer, 2009, BFAST: An alignment tool for large scale genome resequencing, PLoS ONE 4(11):e7767, 12 pages.
Housley, 2009, SNP discovery and haplotype analysis in the segmentally duplicated DRD5 coding region, Ann Hum Genet 73(3):274-282.
Huang, 2008, Comparative analysis of common CFTR polymorphisms poly-T, TGrepeats and M470V in a healthy Chinese population, World J Gastroenterol 14(12):1925-30.
Husemann, 2009, Phylogenetic Comparative Assembly, Algorithms in Bioinformatics: 9th International Workshop, Salzberg & Warnow, Eds. Springer-Verlag, Berlin, Heidelberg, pp. 145-156,.
Illumina, 2010, De Novo assembly using Illumina reads, Technical Note, 8 pages.
International Human Genome Sequencing Consortium, 2004, Finishing the euchromatic sequence of the human genome, Nature 431:931-945.
Iqbal, 2012, De novo assembly and genotyping of variants using colored de Bruijn graphs, Nature Genetics 44:226-232.
Isosomppi, 2009, Disease-causing mutations in the CLRN1 gene alter normal CLRN1 protien trafficking to the plasma membrane, Mol Vis 15:1806-1818.
Jaijo, 2010, Microarray-based mutation analysis of 183 Spanish families with Usher syndrome, Invest Ophthalmol Vis Sci 51(3):1311-7.
Jares, 2006, Genomic platforms for cancer research: potential diagonistic and prognastic applications in clinical oncology, Clin Transl Oncol, 8(3):161-72.
Jensen, 2001, Orthologs and paralogs—we need to get it right, Genome Biol 2(8):1002-1002.3.
Johnson, 2005, Dark matter in the genome: evidence of widespread transcription detected by microarray tiling experiments, Trends in Genetics, 21(2):93-102.
Jones, 2008, Core signaling pathways in human pancreatic cancers revealed by global genomic analyses, Science 321(5897):1801-1806.
Kambara, 1988, Optimization of Parameters in a DNA Sequenator Using Fluorescence Detection, Nature Biotechnology 6:816-821.
Kennedy, 2013, Accessing more human genetic variation with short sequencing reads, American Society of Human Genetics 63rd Annual Meeting, Abstract, Oct. 22, 2013, 2 pages.
Kent, 2002, BLAT-The BLAST-like alignment tool, Genome Res 12(4): 656-664.
Kerem, 1989, Identification of the cystic fibrosis gene: genetic analysis, Science 245:1073-1080.
Kinde, 2012, FAST-SeqS: a simple an effective method for detection of aneuploidy by massively parallel sequencing, PLoS One 7(7):e41162, 8 pages.
Kircher, 2010, High-througput DNA sequencing—concepts and limitations, Bioassays 32:524-36.
Kirpekar, 1994, Matrix assisted laser desorption/ionization mass spectrometry of enzymatically synthesized RNA up to 150 kDa, Nucl Acids Res 22:3866-3870.
Klein, 2011, LOCAS—A low coverage sequence assembly tool for re-sequencing projects, PLoS One 6(8):e23455, 10 pages.
Kneen, 1998, Green fluorescent protein as a noninvasive intracellular pH indicator, Biophys J 74(3):1591-99.
Koboldt, 2009, VarScan: variant detection in massively parallel sequencing of individual and pooled samples, Bioinformatics 25:2283-85.
Kotsch, 1999, Sequencing of HLA class II genes based on the conserved diversity of the non-coding regions: sequencing based typing of HLA-DRB genes, Tissue Antigens, 53:486-497.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125(2):219-229.

(56) References Cited

OTHER PUBLICATIONS

Krishnakumar, 2008, A comprehensive assay for targeted multiplex amplification of human DNA sequences, PNAS 105:9296-301.
Kumar, 2010, Comparing de novo assemblers for 454 transcriptome data, Genomics 11:571 (12 pages).
Kurtz, 2004, Versatile and open software for comparing large genomes, Genome Biol 5:R12, 9 pages.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25, 10 pages.
Larkin, 2007, Clustal W and Clustal X version 2.0, Bioinformatics, 23(21):2947-2948.
Lecompte, 2001, Multiple alignment of complete sequences (MACS) in the post-genomic era, Gene 270(1-2):17-30.
Li, 2003, DNA binding and cleavage by the periplasmic nuclease Vvn: a novel structure with a known active site, EMBO J 22(15):4014-4025.
Li, 2005, Detection of paternally inherited fetal point mutations for beta-thalassemia using size-fractionated cell-free DNA in maternal plasma, J Amer Med Assoc 293:843-849.
Li, 2008, SOAP: short oligonucleotide alignment program, Bioinformatics 24(5):713-14.
Li, 2009, Fast and accurate short read alignment with Burrows-Wheeler transform, Bioinformatics, 25 (14):1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, Fast and accurate long-read alignment with Burrows-Wheeler transform, Bioinformatics 26(5):589-95.
Li, 2011, Improving SNP discovery by base alignment quality, Bioinformatics 27:1157, 2 pages.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539, 6 pages.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31, 11 pages.
Smirnov, 1996, Sequencing oligonucleotides by exonuclease digestion and delayed extraction matrix-assisted laser desorption ionization time-of-flight mass spectrometry, Anal Biochem 238:19-25.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 2010, Highly-multiplexed barcode sequencing: an efficient method for parallel analysis of pooled samples, Nucleic Acids Research 38(13):e142, 8 pages.
Soni, 2007, Progress toward ultrafast DNA sequencing using solid-state nanopores. Clin Chem, 53(11):1996-2001.
Sonnhammer, 2002, Orthology, paralogy and proposed classification for paralog subtypes, Trends in Genetics, 18(12):619-620.
Spanu, 2010, Genome expansion and gene loss in powdery mildew fungi reveal tradeoffs in extreme parasitism, Science 330(6010):1543-46.
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Streit, 2003, CFTR gene: molecular analysis in patients from South Brazil, Molecular Genetics and Metabolism 78:259-264.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Summerer, 2010, Targeted High Throughput Sequencing of a Cancer-Related Exome Subset by Specific Sequence Capture With a Fully Automated Microarray Platform, Genomics 95(4):241-246.
Sunnucks, 1996, Microsatellite and chromosome evolution of parthenogenetic sitobion aphids in Australia, Genetics 144:747-756.
Tan, 2014, Clinical outcome of preimplantation genetic diagnosis and screening using next generation sequencing, GigaScience 3(30):1-9.
Tarhini, 2018, Predictive and on-treatment monitoring biomarkers in advanced melanoma: Moving toward personalized medicine, Cancer Treatment Reviews, 71:8-18.
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500, 10 pages.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217, 10 pages.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration, Brief Bioinform 24(2):178-92.
Tijssen, 1993, Hybridization with Nucleic Acid Probes—Laboratory Technique in Biochemistry and Molecular Biology (Parts I and II), Elsevier.
Tkachuk, 1990, Detection of bcr-abl Fusion in Chronic Myelogeneous Leukemia by in Situ Hybridization, Science 250:559-562.
Tobler, 2005, The SNPlex Genotyping System: A Flexible and Scalable Platform for SNP Genotyping, J Biomol Tech 16(4):398-406.
Tokino, 1996, Characterization of the human p57 KIP2 gene: alternative splicing, insertion/deletion polymorphisms in VNTR sequences in the coding region, and mutational analysis, Human Genetics 96:625-31.
Treangen, 2011, Repetitive DNA and next-generation sequencing: computational challenges and solutions, Nat Rev Gen 13(1):36-46.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013, 2 pages.
Umbarger, 2014, Next-generation carrier screening, Gen Med 16(2):132-140.
Veeneman, 2012, Oculus: faster sequence alignment by streaming read compression, BMC Bioinformatics 13:297, 8 pages.
Wahl, 1979, Efficient transfer of large DNA fragments from agarose gels to diazobenzyloxymethyl-paper and rapid hybridization by using dextran sulfate, PNAS 76:3683-3687.
Wallace, 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.
Wang, 2005, Allele quantification using molecular inversion probes (MIP), Nucleic Acids Res 33(21):e183, 14 pages.
Wang, 2007, Analysis of molecular inversion probe performance for allele copy number determination, Genome Biology, 8(11):R246.1-R246.14.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988, 20 pages.

(56) References Cited

OTHER PUBLICATIONS

Watson, 2004, Cystic fibrosis population carrier screening: 2004 revision of American College of Medical Genetics mutation panel, Genetics in Medicine 6(5):387-391.
Williams, 2003, Restriction endonucleases: classification, properties, and applications, Mol Biotechnol 23(3):225-43.
Wirth, 1999, Quantitative analysis of survival motor neuron copies, Am J Hum Genet 64:1340-1356.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973-7979.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Ku, 2012, FastUniq: A fast de novo duplicates removal tool for paired short reads, PLoS One 7(12):e52249, 6 pages.
Yau, 1996, Accurate diagnosis of carriers of deletions and duplications in Duchenne/Becker muscular dystrophy by fluorescent dosage analysis, J Med Gen 33(7):550-8.
Li, 2011, Single nucleotide polymorphism genotyping and point mutation detection by ligation on microarrays, J Nanosci Nanotechnol 11(2):994-1003.
Li, 2012, A new approach to detecting low-level mutations in next-generation sequence data, Genome Biol 13:1-15.
Li, 2014, HUGO: Hierarchical mUlti-reference Genome Compression for aligned reads, JAMIA 21:363-373.
Lin, 2008, ZOOM! Zillions of Oligos Mapped, Bioinformatics 24:2431-2437.
Lin, 2010, A molecular inversion prove assay for detecting alternative splicing, BMC Genomics 11(712):1-14.
Lin, 2012, Development and evaluation of a reverse dot blot assay for the simultaneous detection of common alpha and beta thalassemia in Chinese, Blood Cells Molecules, and Diseases 48(2):86-90.
Lipman, 1985, Rapid and sensitive protein similarity searches, Science 227(4693):1435-41.
Liu, 2012, Comparison of next-generation sequencing systems, J Biomed Biotech 2012:251364, 12 pages.
Llopis, 1998, Measurement of cytosolic, mitochondrial, and Golgi pH in single living cells with green fluorescent proteins, PNAS 95(12):6803-08.
Ma, 2006, Application of real-time polymerase chain reaction (RT-PCR), J Am Soc 1-15.
MacArthur, 2014, Guidelines for investigating causality of sequence variants in human disease, Nature 508:469-76.
Maddalena, 2005, Technical standards and guidelines: molecular genetic testing for ultra-rare disorders, Genet Med 7:571-83.
Malewicz, 2010, Pregel: a system for large-scale graph processing, Proc. ACM SIGMOD Int Conf Mgmt Data 135-46.
Mamanova, 2010, Target-enrichment strategies for next-generation sequencing, Nat Meth 7(2):111-118.
Margulies, 2005, Genome sequencing in micro-fabricated high-density picotiter reactors, Nature, 437:376-380.
Marras, 1999, Multiplex detection of single-nucleotide variations using molecular beacons, Genetic Analysis: Biomolecular Engineering 14:151, 6 pages.
Maxam, 1977, A new method for sequencing DNA, Proc Natl Acad Sci 74(2):560-564.
Maxam, 1977, A new method for sequencing DNA, PNAS, 74:560-564.
May 1988, How Many Species Are There on Earth?, Science 241(4872):1441-9.
McDonnell, 2007, Antisepsis, disinfection, and sterilization: types, action, and resistance, p. 239.
McKenna, 2010, The Genome Analysis Toolkit: A MapReduce framework for analyzing next-generation DNA sequencing data, Genome Research 20:1297-1303.
Messiaen, 1999, Exon 10b of the NF1 gene represents a mutational hotspot and harbors a recurrent missense mutation Y489C associated with aberrant splicing, Genetics in Medicine, 1(6):248-253.
Meyer, 2007, Targeted high-throughput sequencing of tagged nucleic acid samples, Nucleic Acids Research 35(15):e97, 5 pages.
Meyer, 2008, Parallel tagged sequencing on the 454 platform, Nat Protocol 3(2):267-278.
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Mills, 2010, Mapping copy number variation by population-scale genome sequencing, Nature 470(7332):59-65.
Miner, 2004, Molecular barcodes detect redundancy and contamination in hairpin-bisulfite PCR, Nucl Acids Res 32(17):e135, 4 pages.
Minton, 2011, Mutation Surveyor: software for DNA sequence analysis, Meth Mol Biol 688:143-53.
Miyake, 2009, PIK3CA gene mutations and umplification in uterine cancers, Canc Lett 261:120-126.
Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, DELIMINATE—a fast and efficient methods for loss-less compression of genomice sequences, Bioinformatics 28(19):2527-2529.
Monani, 1999, A single nucleotide difference that alters splicing patterns distinguishes the SMA gene SMN1 from the copy gene SMN2, Human Molecular Genetics 8(7):1177-1183.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment-the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single pase pair mutations, Nucl Acids Res 17(18):7187-7194.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen, 1999, Peptide Nucleic Acids, Protocols and Applications (Norfolk: Horizon Scientific Press, 1-19).
Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nordoff, 2003, Ion stablility of nucleic acids in infrared matrix-assisted laser desorption/ionization mass spectrometry, Nucl Acid Res 21(5):3347-3357.
Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prot 9(6):1496-1513.

* cited by examiner

METHODS FOR COPY NUMBER DETERMINATION

FIELD OF THE INVENTION

The present invention relates generally to genetic testing, and, more particularly, to methods for determining carrier or disease status with respect to a particular disease or condition.

BACKGROUND

Spinal muscular atrophy (SMA) is a lethal autosomal recessive neuromuscular disorder caused by functional loss of the SMN1 gene. The high carrier rate of about 1 in 40 is attributable primarily to SMN1 copy number loss. Copy number loss is attributable to either: deletion of all or part of SMN1; or conversion of SMN1 to SMN2, a linked paralog that encodes an identical protein but is poorly expressed due to a silent coding variant that disrupts proper splicing. Clinical SMA carrier screening typically involves the assessment of the copy number status of SMN1 in manner that distinguishes between SMN1 and SMN2. The most-common screen interrogates the functional exon 7 variant. A screen for a non-functional variant in exon 8 may also be used. However, that variant is not perfectly linked to exon 7, resulting in decreased sensitivity and specificity relative to the exon 7-based screen.

SUMMARY

The invention provides methods for copy number determination for SMN1 with high sensitivity and specificity. The invention allows inference of SMN1 copy number status in a manner that distinguishes SMN1 and SMN2 as a screen for SMA. The invention is based upon the recognition that there are two variants in intron 7 of SMN1 and SMN2, between exons 7 and 8, that are linked to the exon 7 variant typically used in SMA screening assays. According to the invention, the SMN1 and SMN2 copy numbers at the two intron 7 variants are determined. Due to the tight linkage between those variants and the exon 7 variant, the copy number of the entire SMN1 and/or SNM2 gene(s) (or the exon 7 variant) is inferred with high sensitivity and specificity. The inferred copy number is indicative of SMA carrier status. Thus, instead of using the exon 7 variant itself to measure copy number in SMN1/SMN2, the invention provides an inferential measure of SMN1 and/or SMN2 copy number by measuring the intron 7 variants and that provides a sensitivity and specificity on par with those of the direct exon 7 measurements.

In another aspect, the invention provides methods for determining SMA carrier status by combining copy number determination in one or both exon-7-linked variants in intron 7 of SMN1 and/or SMN2 with copy number of the exon 7 variant itself in order to further increase sensitivity and specificity over methods relying only on exon 7 and/or exon 8 variant copy number.

In a preferred embodiment of the invention, the intron 7 variants of SMN1 and SMN2 are dbSNP137 rsID variants rs212214 (hg 19 coordinates chr5:70247921 (SMN1) and chr5:69372616 (SMN2)) and rs212213 (hg19 coordinates chr5:70248036 (SMN1) and chr5:69372616 (SMN2)). Additionally, or alternatively, in a preferred embodiment, the linked exon 7 mutation is on chromosome 5q13.2, with coordinates (GRCh37: 5:69,345,349-69,373,421 (corresponding to dbSNP137 rsID variants rs121909192, rs104893923, or rs76163360).

Methods of the invention comprise capturing a plurality of variants in SMN1/SMN2 intron 7 that are linked to an exon 7 variant, the copy number of which is known or suspected to be associated with SMA carrier status. Captured DNA is sequenced and copy number is estimated based upon the sequence reads, as described in greater detail below.

DETAILED DESCRIPTION

Figure 1:
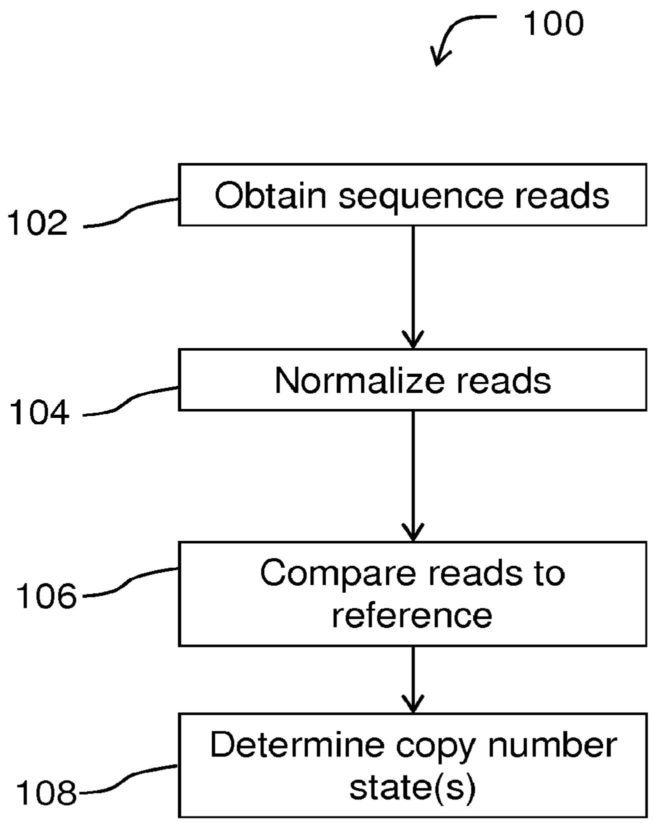
FIG. 1 is a diagram of methods of the invention.

The invention generally relates to methods for determining carrier status for an autosomal recessive disease. The invention is based upon the measurement of copy number in one or more loci that are linked to a locus that is diagnostic for carrier status and, based upon copy number of the one or more loci, inferring copy number of the diagnostic locus. In preferred embodiments, the autosomal recessive trait is SMA and the diagnostic locus in in exon 7 of the SMN1 and/or SMN2 gene. Also in a preferred embodiment, the measured loci are variants in intron 7 between exons 7 and 8. Methods of the invention allow inference of the diagnostic locus by virtue of copy number measurement of reference loci that are tightly-linked to the diagnostic locus.

The invention allows inference of SMN1 copy number status in a manner that distinguishes SMN1 and SMN2 as a screen for SMA. The invention is based upon the recognition that there are two variants in intron 7 of SMN1 and SMN2, between exons 7 and 8, that are linked to the exon 7 variant typically used in SMA screening assays. According to the invention, the SMN1 and SMN2 copy numbers at the two intron 7 variants are determined. Due to the tight linkage between those variants and the exon 7 variant, the copy number of the entire SMN1 and/or SNM2 gene(s) (or the exon 7 variant) is inferred with high sensitivity and specificity. The inferred copy number is indicative of SMA carrier status. Thus, instead of using the exon 7 variant itself to measure copy number in SMN1/SMN2, the invention provides an inferential measure of SMN1 and/or SMN2 copy number by measuring the intron 7 variants and that provides a sensitivity and specificity on par with those of the direct exon 7 measurements.

In another aspect, the invention provides methods for determining SMA carrier status by combining copy number determination in one or both exon-7-linked variants in intron 7 of SMN1 and/or SMN2 with copy number of the exon 7 variant itself in order to further increase sensitivity and specificity over methods relying only on exon 7 and/or exon 8 variant copy number.

In a preferred embodiment of the invention, the intron 7 variants of SMN1 and SMN2 are dbSNP137 rsID variants rs212214 (hg 19 coordinates chr5:70247921 (SMN1) and chr5:69372616 (SMN2)) and rs212213 (hg19 coordinates chr5:70248036 (SMN1) and chr5:69372616 (SMN2)). Additionally, or alternatively, in a preferred embodiment, the linked exon 7 mutation is on chromosome 5q13.2, with coordinates (GRCh37: 5:69,345,349-69,373,421 (corresponding to dbSNP137 rsID variants rs121909192, rs104893923, or rs76163360).

One way in which methods of the invention are implemented is by capturing and sequencing reference locus DNA that binds to molecular inversion probes. Generally, capturing and isolating reference locus DNA from a sample involves conducting an assay that uses molecular inversion probes. A molecular inversion probe is composed of a common linker sequence and two unique targeting arms that hybridize to genomic regions flanking a target. In a capture protocol, probes are tiled across a region of a nucleic acid template to ensure overlapping coverage. The hybridized probes are then filled-in with polymerase and the circularized probe is closed with ligase. Following circularization of the probes, the remaining linear (un-captured) genomic DNA is digested away with exonuclease (leaving only the captured targets within the circularized probes). The probes are then sequenced and sequence data is assembled together. That assembled sequence is analyzed for mutations.

Sequencing may be any technique known in the art, such as sequencing-by-synthesis and single molecule sequencing-by-synthesis. However, any sequencing platform may be used with methods of the invention. In some embodiments, the probes are amplified prior to sequencing. In other embodiments, the probes are sequenced without prior amplification. Commercially available sequencing instruments are sold by Illumina, Roche, 454 Life Sciences, and Life Technologies.

If sequencing is used as the analysis method, then the probes can undergo a standard sequencing workflow prior to being sequencing. Such workflow may involve attaching barcodes and/or sequencing adaptors to the probes prior to sequencing. The probes may or may not be attached to a solid support for sequencing. Exemplary solid supports are flow cells, beads, or any planar substrate.

The analysis method is used to determine the copy number of which is known or suspected to be associated with SMA carrier status, wherein the copy number is estimated based upon the sequence reads.

Nucleic acids suitable for use in aspects of the invention include but are not limited to genomic DNA, genomic RNA, synthesized nucleic acids, whole or partial genome amplification product, and high molecular weight nucleic acids, e.g. individual chromosomes. Genomic DNA and genomic RNA constitute the total genetic information of an organism. Genomic nucleic acids molecules are generally large, and in most organisms are organized into DNA-protein complexes called chromosomes, which the exception of viruses that have RNA genomes. Genomic RNA also includes, for example, RNA transcribed from DNA, unprocessed transcripts, mRNAs, and cDNAs. Sometimes the quality and quantity of genomic nucleic acids obtained from samples precludes their usefulness in large scale genotyping studies. To overcome this problem, use of whole genome amplification products and partial genome amplification products allows for characterization of the genome of a sample even if the quantity and quality of the genomic nucleic acid is limited.

Samples and Obtaining Nucleic Acid

In certain aspects, methods of the invention may involve obtaining a sample. The sample is typically a tissue or body fluid that is obtained in any clinically acceptable manner. A tissue is a mass of connected cells and/or extracellular matrix material, e.g. skin tissue, endometrial tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed. Samples are also obtained from the environment (e.g., air, agricultural, water and soil); and research samples (e.g., products of a nucleic acid amplification reaction, or purified genomic DNA, RNA, proteins, etc.).

Isolation, extraction or derivation of genomic nucleic acids is performed by methods known in the art. Isolating nucleic acid from a biological sample generally includes treating a biological sample in such a manner that genomic nucleic acids present in the sample are extracted and made available for analysis. Any isolation method that results in extracted/isolated genomic nucleic may be used in the practice of the present invention.

Nucleic acids may be obtained by methods known in the art. Generally, nucleic acids are extracted using techniques, such as those described in Sambrook, J., Fritsch, E. F., and Maniatis, T. (1989) Molecular Cloning: A Laboratory Manual. 2nd ed. Cold Spring Harbor, NY: Cold Spring Harbor Laboratory), the contents of which are incorporated by reference herein. Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.), Autogen (Holliston, MA); Beckman Coulter (Brea, CA), (AutoGenFlex STAR robot with Qiagen FlexiGene chemistry. For example, Autogen manufactures FlexStar automated extraction kits used in combination with Qiagen FlexiGene Chemistry, and Beckeman Coulter manufactures Agencourt GenFind kits for bead-based extraction chemistry. User Guides that describe in detail the protocol(s) to be followed are usually included in all these kits, for example, Qiagen's literature for their PureGene extraction chemistry entitled "Qiagen PureGene Handbook" 3rd Edition, dated June 2011.

After cells have been obtained from the sample, it is preferable to lyse cells in order to isolate genomic nucleic acid. Cellular extracts can be subjected to other steps to drive nucleic acid isolation toward completion by, e.g., differential precipitation, column chromatography, extraction with organic solvents and the like. Extracts then may be further treated, for example, by filtration and/or centrifugation and/or with chaotropic salts such as guanidinium isothiocyanate or urea or with organic solvents such as phenol and/or CHCl3 to denature any contaminating and potentially interfering proteins. The genomic nucleic acid can also be resuspended in a hydrating solution, such as an aqueous buffer. The genomic nucleic acid can be suspended in, for example, water, Tris buffers, or other buffers. In certain embodiments the genomic nucleic acid can be re-suspended in Qiagen DNA hydration solution, or other Tris-based buffer of a pH of around 7.5.

Depending on the type of method used for extraction, the genomic nucleic acid obtained can vary in size. The integrity and size of genomic nucleic acid can be determined by pulse-field gel electrophoresis (PFGE) using an agarose gel.

In addition to genomic nucleic acids, whole genome amplification product and partial genomic amplification products can be used in aspects of the invention. Methods of obtaining whole genome amplification product and partial genome amplification product are described in detail in Pinter et al. U.S. Patent Publication Number 2004/0209299, and include, for example, generally ligation mediated PCR™, random primed PCR™, strand displacement mediated PCR™, and cell immortalization.

In certain embodiments, a genomic sample is collected from a subject followed by enrichment for genes or gene fragments of interest, for example by hybridization to a nucleotide array. The sample may be enriched for genes of interest using methods known in the art, such as hybrid capture. See for examples, Lapidus (U.S. Pat. No. 7,666,593), the content of which is incorporated by reference herein in its entirety. As will be described in more detail below, a preferable capture method uses molecular inversion probes.

In certain embodiments, the body fluid sample is maternal blood. The maternal blood sample typically will include cell free circulating nucleic acid. That nucleic acid can be a mixture of maternal nucleic acid and fetal nucleic acid from a fetus that is being carried by the subject. Methods for extracting fetal nucleic acid from maternal blood are described for example in Li et al. (J. Amer. Med. Assoc. 293:843-849, 2005) and Lapidus et al. (U.S. patent application publication number 2010/0216151), the content of each of which is incorporated by reference herein its entirety.

In certain embodiments, the sample is a body fluid sample that includes cell free circulating DNA. The sample can be from a male or a female. Cell death, e.g., due to cancer, results in nucleic acid from that cell being shed into the blood stream. That nucleic acid includes the cancerous mutations, and analyzing such nucleic acid provides insight into the subject's cancer.

Fragmenting the Nucleic Acid

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Technique in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. In one embodiment, the genomic nucleic acid fragments can range from 1 kilobases to 20 kilobases. Fragments can vary in size and have an average fragment length of about 10 kilobases. However, desired fragment length and ranges of fragment lengths can be adjusted depending on the type of nucleic acid targets one seeks to capture and the design and type of MIP probes. The particular method of fragmenting is selected to achieve the desired fragment length. Numerous non-limiting examples are provided below.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to effect differing amounts of shearing (and therefore varying length distributions).

In one aspect, a nucleic acid is fragmented by heating a nucleic acid immersed in a buffer system at a certain temperature for a certain period to time to initiate hydrolysis and thus fragment the nucleic acid. The pH of the buffer system, duration of heating, and temperature can be varied to achieve a desired fragmentation of the nucleic acid. In one embodiment, after a genomic nucleic acid is purified, it is resuspended in a Tris-based buffer at a pH between 7.5 and 8.0, such as Qiagen's DNA hydrating solution. The resuspended genomic nucleic acid is then heated to 65° C. and incubated overnight (about 16-24 hours) at 65° C. Heating shifts the pH of the buffer into the low- to mid-6 range, which leads to acid hydrolysis. Over time, the acid hydrolysis causes the genomic nucleic acid to fragment into single-stranded and/or double-stranded products.

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids or strong bases.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH ([OH—] concentration to 0.1 N) is added, and the sample is stirred until the DNA redissolves completely. The sample is then incubated at 65° C. for 30 minutes in order to hydrolyze the DNA. Resulting fragments typically range from about 250-1000 nucleotides but can vary lower or higher depending on the conditions of hydrolysis.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124(27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8): 1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi: 10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oefner et al., Nucleic Acids Res. 1996; Thorstenson et al., Genome Res. 1995). This technique is based on point-sink hydrodynamics that result when a nucleic acid sample is forced through a small hole by a syringe pump.

In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonification is described in U.S. Patent Publication 2009/0233814. In the method, a purified nucleic acid is obtained placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948,843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with Diagonnode's BioRuptor®. Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing the nucleic acid in to fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts RJ (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Kruger D H (June 1993). "Biology of DNA restriction". Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams RJ (2003). "Restriction endonucleases: classification, properties, and applications". Mol. Biotechnol. 23 (3): 225-43.

Where restriction endonucleases recognize specific sequencings in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

Denaturing the Nucleic Acids

Methods of the invention also provide for denaturing nucleic acid to render the nucleic acid single stranded for hybridization to a capture probe, such as a MIP probe. Denaturation can result from the fragmentation method chosen, as described above. For example, one skilled in the art recognizes that a genomic nucleic acid can be denatured during pH-based shearing or fragmenting via nicking endonucleases. Denaturation can occur either before, during, or after fragmentation. In addition, the use of pH or heat during the fragmenting step can result in denatured nucleic acid fragments. See, for example, McDonnell, "Antisepsis, disinfection, and sterilization: types, action, and resistance," pg. 239 (2007).

Heat-based denaturing is the process by which double-stranded deoxyribonucleic acid unwinds and separates into single-stranded strands through the breaking of hydrogen bonding between the bases. Heat denaturation of a nucleic acid of an unknown sequence typically uses a temperature high enough to ensure denaturation of even nucleic acids having a very high GC content, e.g., 95° C.-98° C. in the absence of any chemical denaturant. It is well within the abilities of one of ordinary skill in the art to optimize the conditions (e.g., time, temperature, etc.) for denaturation of the nucleic acid. Temperatures significantly lower than 95° C. can also be used if the DNA contains nicks (and therefore sticky overhangs of low Tm) or sequence of sufficiently low Tm.

Denaturing nucleic acids with the use of pH is also well known in the art, and such denaturation can be accomplished using any method known in the art such as introducing a nucleic acid to high or low pH, low ionic strength, and/or heat, which disrupts base-pairing causing a double-stranded helix to dissociate into single strands. For methods of pH-based denaturation see, for example, Dore et al. Biophys J. 1969 November; 9(11): 1281-1311; A. M. Michelson The Chemistry of Nucleosides and Nucleotides, Academic Press, London and New York (1963).

Nucleic acids can also be denatured via electro-chemical means, for example, by applying a voltage to a nucleic acid within a solution by means of an electrode. Varying methods of denaturing by applying a voltage are discussed in detail in U.S. Pat. Nos. 6,197,508 and 5,993,611.

Molecular Inversion Probe Capture

Any method known in the art for capturing target sequences may be used with methods of the invention. In certain embodiments, molecular inversion probes (MIP) are used with methods of the invention and an oligonucleotide-driven annealing reaction is performed between genomic DNA and target-specific probes to form open loop complexes, where the target sequence is flanked by the ends of each oligo. Then, polymerase and ligase enzymes are added to fill and seal the gap between the two oligonucleotide probe ends, forming a covalently-closed circular molecule that contains the target sequence. Finally, an exonuclease mix is added to degrade any non-circular DNA (un-reacted probe, genomic DNA). What remains is circular DNA containing the set of targets captured by the reaction. Further details are provided for example in the following U.S. Pat. Nos. 5,866,337; 7,790,388; 6,858,412; 7,993,880; 7,700,323; 6,558,928; 6,235,472; 7,320,860; 7,351,528; 7,074,564; 5,871,921; 7,510,829; 7,862,999; and 7,883,849, the content of each of which is incorporated by reference herein in its entirety. Molecular inversion probes and methods for using such probes is further described, for example in Porreca et al. (Internal patent application publication number WO 2010/126614), the content of which is incorporated by reference herein in its entirety.

Molecular inversion probe technology is used to detect or amplify particular nucleic acid sequences in complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes.

In certain embodiments, molecular inversion probes include a universal portion flanked by two unique targeting arms. The targeting arms are designed to hybridize immediately upstream and downstream of a specific target sequence located on a genomic nucleic acid fragment. The molecular inversion probes are introduced to nucleic acid fragments to perform capture of target sequences located on the fragments. According to the invention, fragmenting aids in capture of target nucleic acid by molecular inversion probes.

After capture of the target sequence (e.g., locus) of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat Methods. 2009 Apr. 6: 1-2).

In one embodiment of the present invention, a library of molecular inversion probes is generated, wherein the probes are used in capturing DNA of genomic regions of interests (e.g., SMN1, SMN2, control DNA). The library consists of a plurality of SMA oligonucleotide probes capable of capturing one or more genomic regions of interest (e.g., SMN1, SMN2, and control loci) within the samples to be tested.

The result of MIP capture as described above is a library of circular target probes, which then can be processed in a variety of ways. In one aspect, adaptors for sequencing can be attached during common linker-mediated PCR, resulting in a library with non-random, fixed starting points for sequencing. In another aspect, for preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

It should be appreciated that aspects of the invention can involve varying the amounts of genomic nucleic acid and varying the amounts of MIP probes to reach a customized result. In some embodiments, the amount of genomic nucleic acid used per subject ranges from 1 ng to 10 μg (e.g., 500 ng to 5 μg). However, higher or lower amounts (e.g., less than 1 ng, more than 10 μg, 10-50 μg, 50-100 μg or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some embodiments, it should be appreciated that one or more intervening sequences (e.g., sequence between the first and second targeting arms on a MIP capture probe), identifier or tag sequences, or other probe sequences that are not designed to hybridize to a target sequence 30 (e.g., a genomic target sequence) should be designed to avoid excessive complementarity (to avoid cross-hybridization) to target sequences or other sequences (e.g., other genomic sequences) that may be in a biological sample. For example, these sequences may be designed to have a sufficient number of mismatches with any genomic sequence (e.g., at least 5, 10, 15, or more mismatches out of 30 bases) or to have a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some embodiments, probes or regions of probes or other nucleic acids are described herein as including certain sequences or sequence characteristics (e.g., length, other properties, etc.). In addition, components (e.g., arms, central regions, tags, primer sites, etc., or any combination thereof) of such probes can include certain sequences or sequence characteristics that consist of one or more characteristics (e.g., length or other properties, etc.).

It should be appreciated that probes, primers, and other nucleic acids designed or used herein may be synthetic, natural, or a combination thereof. Accordingly, as used herein, the term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" may be used interchangeably and refer to oligoribonucleotides as well as oligodeoxyribonucleotides. The terms shall also include polynucleosides (i.e., a polynucleotide minus a phosphate) and any other organic base containing nucleic acid.

The organic bases include adenine, uracil, guanine, thymine, cytosine and inosine. Unless otherwise stated, nucleic acids may be single or double stranded. The nucleic acid may be naturally or non-naturally occurring. Nucleic acids can be obtained from natural sources, or can be synthesized using a nucleic acid synthesizer (i.e., synthetic).

Harvest and isolation of nucleic acids are routinely performed in the art and suitable methods can be found in standard molecular biology textbooks. (See, for example, Maniatis' Handbook of Molecular Biology). The nucleic acid may be DNA or RNA, such as genomic DNA, mitochondrial DNA, mRNA, cDNA, rRNA, miRNA, or a combination thereof. Non-naturally occurring nucleic acids such as bacterial artificial chromosomes (BACs) and yeast artificial chromosomes (YACs) can also be used.

The invention also contemplates the use of nucleic acid derivatives. As will be described herein, the use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, phosphorothiolate modifications, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they may include nucleic acids having backbone sugars which are covalently attached to low molecular weight organic groups other than a hydroxyl group at the 3' position and other than a phosphate group at the 5' position (e.g., an 2'-0-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, substitution(s) may include one or more substitutions/modifications in the sugars/bases, groups attached to the base, including biotin, fluorescent groups (fluorescein, cyanine, rhodamine, etc), chemically-reactive groups including carboxyl, NHS, thiol, etc., or any combination thereof.

A nucleic acid may be a peptide nucleic acid (PNA), locked nucleic acid (LNA), DNA, RNA, or co-nucleic acids of the same such as DNA-LNA co-nucleic acids. PNA are DNA analogs having their phosphate backbone replaced with 2-aminoethyl glycine residues linked to nucleotide bases through glycine amino nitrogen and methylenecarbonyl linkers. PNA can bind to both DNA and RNA targets by Watson-Crick base pairing, and in so doing form stronger hybrids than would be possible with DNA or RNA based oligonucleotides in some cases.

PNA are synthesized from monomers connected by a peptide bond (Nielsen, P. E. et al. Peptide Nucleic Acids, Protocols and Applications, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNA. Several types of PNA designs exist, and these include single strand PNA (ssPNA), bisPNA and pseudocomplementary PNA (pcPNA).

The structure of PNA/DNA complex depends on the particular PNA and its sequence. ssPNA binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., Biochemistry 36:7973 (1997)).

A locked nucleic acid (LNA) is a modified RNA nucleotide. An LNA form hybrids with DNA, which are at least as stable as PNA/DNA hybrids (Braasch, D. A. et al., Chem & Biol. 8(1):1-7(2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. Peptide Nucleic Acids, Protocols and Applications, Norfolk: Horizon Scientific Press, p. 1-19 (1999)). Also, lesser number of LNA residues in the sequence dramatically improves accuracy of the synthesis. Most of biochemical approaches for nucleic acid conjugations are applicable to LNA/DNA constructs.

While probes have been typically designed to meet certain constraints (e.g. melting temperature, G/C content, etc.) known to partially affect capture/amplification efficiency (Ball et al (2009) Nat Biotech 27:361-8 AND Deng et al (2009) Nat Biotech 27:353-60), a set of constraints which is sufficient to ensure either largely uniform or highly reproducible capture/amplification efficiency has not previously been achieved.

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 bp (as used herein, a bp refers to a base pair on a double-stranded nucleic acid 13 however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is to be appreciated that the length of a capture molecule on a nucleic acid fragment (e.g., a target nucleic acid or subregion thereof) is selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids on a nucleic acid fragment are too large to be captured with one probe. Consequently, it may be necessary to capture multiple subregions of a target nucleic acid in order to analyze the full target.

In some embodiments, a sub-region of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 bp or more. In other embodiments, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 bp or more) longer than corresponding target (e.g., subregion of a target nucleic acid, target nucleic acid). In some embodiments, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid.

Methods of the invention also provide for combining the method of fragmenting the nucleic acid prior to capture with other MIP capture techniques that are designed to increase target uniformity, reproducibility, and specificity. Other MIP capture techniques are shown in co-owned and pending application, U.S. patent application Ser. No. 13/266,862, "Methods and Compositions for Evaluating Genetic Markers."

For example, multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted by changing the number of different MIPs used to capture a given molecule.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Barcode PCR

With these methods, a single copy of a specific target nucleic acid may be amplified to a level that can be sequenced. Further, the amplified segments created by an amplification process such as PCR may be, themselves, efficient templates for subsequent PCR amplifications.

Amplification or sequencing adapters or barcodes, or a combination thereof, may be attached to the fragmented nucleic acid. Such molecules may be commercially obtained, such as from Integrated DNA Technologies (Coralville, IA). In certain embodiments, such sequences are attached to the template nucleic acid molecule with an enzyme such as a ligase. Suitable ligases include T4 DNA ligase and T4 RNA ligase, available commercially from New England Biolabs (Ipswich, MA). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, WI). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, one or more bar code is attached to each, any, or all of the fragments. A bar code sequence generally includes certain features that make the sequence useful in sequencing reactions. The bar code sequences are designed such that each sequence is correlated to a particular portion of nucleic acid, allowing sequence reads to be correlated back to the portion from which they came. Methods of designing sets of bar code sequences is shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides.

In certain embodiments, the bar code sequences are attached to the template nucleic acid molecule, e.g., with an enzyme. The enzyme may be a ligase or a polymerase, as discussed above. Attaching bar code sequences to nucleic acid templates is shown in U.S. Pub. 2008/0081330 and U.S. Pub. 2011/0301042, the content of each of which is incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety. After any processing steps (e.g., obtaining, isolating, fragmenting, amplification, or barcoding), nucleic acid can be sequenced.

Amplification

Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

Methods for performing PCR in droplets are shown for example in Link et al. (U.S. patent application numbers 2008/0014589, 2008/0003142, and 2010/0137163) and Anderson et al. (U.S. Pat. No. 7,041,481 and which reissued as RE41,780), the content of each of which is incorporated by reference herein in its entirety.

Other amplification methods and strategies can also be utilized to detect nucleic acids in biological fluids. For example, another approach would be to combine PCR and the ligase chain reaction (LCR). Since PCR amplifies faster than LCR and requires fewer copies of target DNA to initiate, PCR can be used as first step followed by LCR. The amplified product could then be used in a LCR or ligase detection reaction (LDR) in an allele-specific manner that would indicate if a mutation was present. Another approach is to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) PNAS 88:189-193; Barany F. (1991) PCR Methods and Applications 1:5-16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F. (1991) PNAS 88:189-193). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al. (1990) PNAS 87: 8923-8927).

Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

A sequencing technique that can be used includes, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Another example of DNA sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Sequencing generates a plurality of reads. Reads generally include sequences of nucleotide data less than about 150 bases in length, or less than about 90 bases in length. In certain embodiments, reads are between about 80 and about 90 bases, e.g., about 85 bases in length. In some embodiments, these are very short reads, i.e., less than about 50 or about 30 bases in length.

Data Analysis

The sequence reads are analyzed to determine copy number states of genomic regions of interest. A set of sequence reads can be analyzed by any suitable method known in the art. For example, in some embodiments, sequence reads are analyzed by hardware or software provided as part of a sequence instrument. In some embodiments, individual sequence reads are reviewed by sight (e.g., on a computer monitor). A computer program may be written that pulls an observed genotype from individual reads. In certain embodiments, analyzing the reads includes assembling the sequence reads and then genotyping the assembled reads.

Sequence assembly can be done by methods known in the art including reference-based assemblies, de novo assemblies, assembly by alignment, or combination methods. Assembly can include methods described in U.S. Pat. No. 8,209,130 titled Sequence Assembly by Porecca and Kennedy, the contents of each of which are hereby incorporated by reference in their entirety for all purposes. In some embodiments, sequence assembly uses the low coverage sequence assembly software (LOCAS) tool described by Klein, et al., in LOCAS-A low coverage sequence assembly tool for re-sequencing projects, PLoS One 6(8) article 23455 (2011), the contents of which are hereby incorporated by reference in their entirety. Sequence assembly is described in U.S. Pat. Nos. 8,165,821; 7,809,509; U.S. Pat. No. 6,223,128; U.S. Pub. 2011/0257889; and U.S. Pub. 2009/0318310, the contents of each of which are hereby incorporated by reference in their entirety.

As part of the analysis and determination of copy number states and subsequent identification of copy number variation, the sequence read counts for genomic regions of interest are normalized based on internal controls. In particular, an intra-sample normalization is performed to control for variable sequencing depths between samples. The sequence read counts for each genomic region of interest within a sample will be normalized according to the total read count across all control references within the sample.

After normalizing read counts for both the genomic regions of interest and control references, copy number states may be determined. In one embodiment, the normalized values for each sample of interest will be compared to the normalized values for a control sample. A ratio, for example, may be generated based on the comparison, wherein the ratio is indicative of copy number and further determinative of any copy number variation. In the event that the determined copy number of a genomic region of interest of a particular sample falls within a tolerable level (as determined by ratio between test and control samples), it can be determined that genomic region of interest does not present copy number variation and thus the patient is at low risk for being a carrier of a condition or disease associated with such. In the event that the determined copy number of a genomic region of interest of a particular sample falls outside of a tolerable level, it can be determined that genomic region of interest does present copy number variation and thus the patient is at risk for being a carrier of a condition or disease associated with such.

FIG. 1 is a flow diagram illustrating one embodiment of a method for determining carrier status of an autosomal recessive disease. In particular, upon capturing nucleic acid corresponding to at least one genomic locus that is linked to a genomic locus that is diagnostic for an autosomal recessive disease (e.g., capturing nucleic acid corresponding to genomic locus on intron 7 of an SMN1 or SMN2 gene or both) and further sequencing the captured nucleic acid, sequence reads are further processed as illustrated in FIG. 1. The method 100 includes obtaining sequence reads (operation 102) and normalizing read counts (operation 104). In some embodiments, read counts for a genomic region of interest are normalized with respect to an internal control DNA. The method 100 further includes comparing normalized read counts to the internal control DNA (operation 106), thereby obtaining a ratio. The method further includes determining a copy number state of the genomic region of interest (operation 108) based on the comparison, specifically the ratio.

The plurality of reads generated by the sequencing method described above are analyzed to determine copy number states, and ultimately copy number variation, in any of the genomic regions of interest (e.g., genomic locus on exon 7 of an SMN1 gene, specifically rs212214 and rs212213) that would necessarily indicate the presence of an autosomal recessive trait in which copy number variation is diagnostic (e.g., spinal muscular atrophy). Analysis of the read counts may be carried out using Illumina's HiSeq BclConverter software. Files (e.g., qSeq files) may be generated for both the genomic and barcode reads. In particular, in accordance with one method of the present invention, genomic read data for each sample is split based upon the barcode reads, which yields separate FASTQ files for each sample.

Analysis of the sequence results has a first step of normalizing the read counts for the SMN1 loci and/or SMN2 loci (genetic regions of interest for SMA). The read counts may be normalized by dividing the read counts with a read count sum for a control. Then, the average normalized values for a set of pre-determined or empirically-identified (e.g., by analysis iteration) wild-type control samples may be obtained. Then the normalized read counts for each test sample (each locus) may be compared to the normalized read counts for each of the control samples, thereby obtaining a ratio of normalized read count of test samples/normalized read count of controls.

Based on the ratios, loci copy numbers may be called as follows: a ratio of <0.1 will be called a copy number state of 0; a ratio between 0.1 and 0.8 will be called a copy number state of 1; a ratio between 0.8 and 1.25 will be called a copy number state of 2; and a ratio of >1.25 will be called a copy number state of 3+.

The determined copy numbers can then be used to determine the carrier status of an individual from which the sample was obtained (i.e. whether the patient is a carrier of the disease). In particular, if the copy number state is determined to vary from the normal copy state (e.g., CN is 0, 1 or 3+), it is indicative the condition (e.g., carrier of SMA).

Additionally, or alternatively, upon initial normalization of the read counts for the test samples and control samples, the resulting vector of normalized frequencies may include x=[f1, f2, . . . , fn] which correspond to the frequencies of each of the loci being queried (test and control). The normalized frequencies from either a single control sample or a "synthetic" control (average of multiple control samples) y=[g1, g2, . . . , gn] may be used to calculate the copy number of each locus interrogated c=x./y=[f1/g1, f2/g2, . . . , fn/gn].

Computing Devices and Software

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access the reference set to compare data derived from the female subject to the reference set. In other embodiments, however, the reference set is stored locally within the computer and the computer accesses the reference set within the CPU to compare subject data to the reference set. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

Functions described above can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system 200 for implementing some or all of the described inventive methods can include one or more processors (e.g., a central processing unit (CPU) a graphics processing unit (GPU), or both), main memory and static memory, which communicate with each other via a bus.

Figure 2:
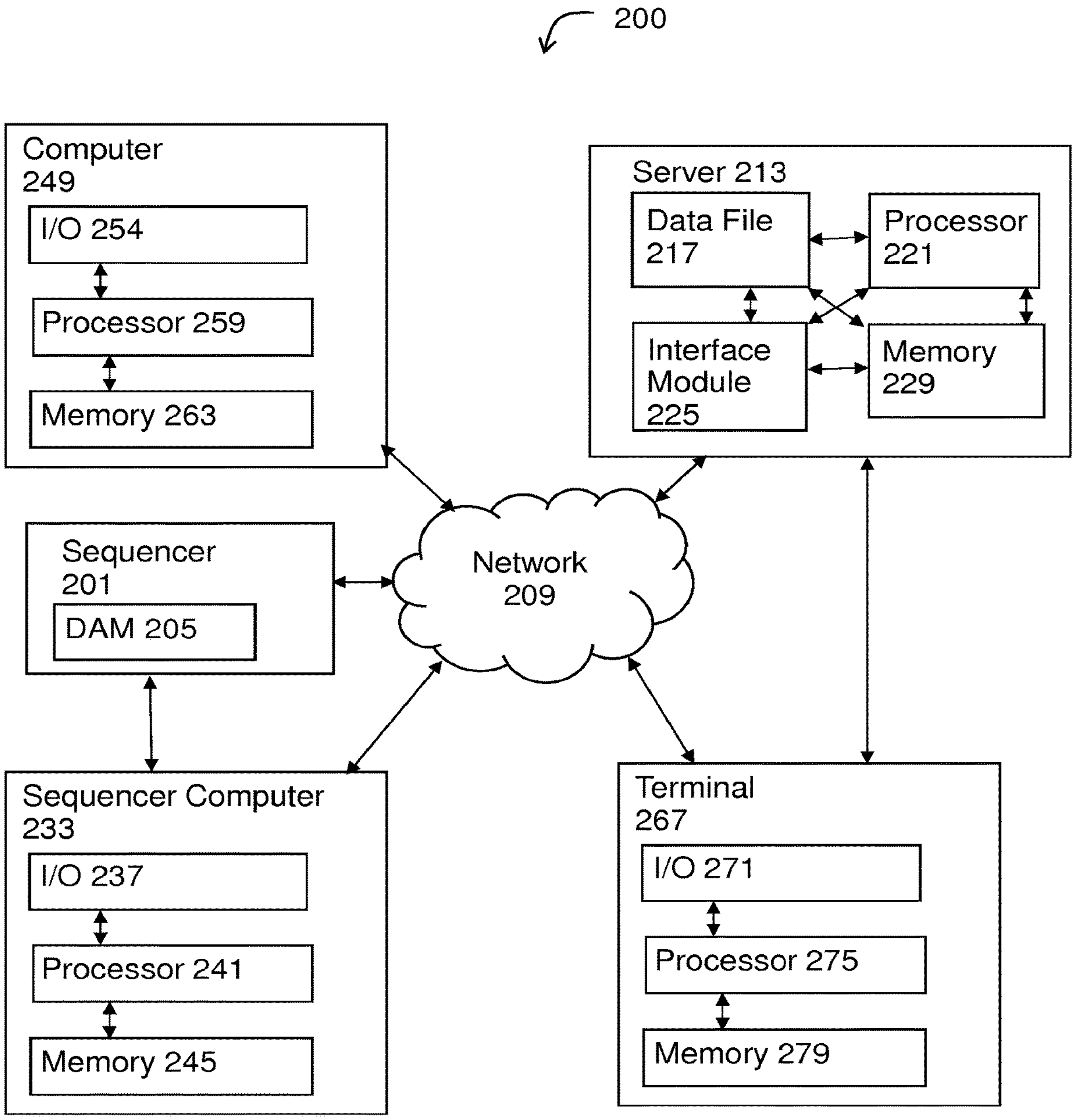
FIG. 2 illustrates a system for performing methods of the invention.

In an exemplary embodiment shown in FIG. 2, system 200 includes a sequencer 201 with a data acquisition module 205 to obtain sequence read data. The sequencer 201 may optionally include or be operably coupled to its own, e.g., dedicated, sequencer computer 233 (including an input/output mechanism 237, one or more of processor 241, and memory 245). Additionally or alternatively, the sequencer 201 may be operably coupled to a server 213 or computer 249 (e.g., laptop, desktop, or tablet) via a network 209. As previously described herein, the sequencer 201 may include the HiSeq 2500/1500 system sold by Illumina, Inc. (San Diego, CA).

The computer 249 includes one or more processors 259 and memory 263 as well as an input/output mechanism 254. Where methods of the invention employ a client/server architecture, steps of methods of the invention may be performed using the server 213, which includes one or more of processors 221 and memory 229, capable of obtaining data, instructions, etc., or providing results via an interface module 225 or providing results as a file 217. The server 213 may be engaged over the network 209 by the computer 249 or the terminal 267, or the server 213 may be directly connected to the terminal 267, which can include one or more processors 275 and memory 279, as well as an input/output mechanism 271.

The system or machines 200 according to the invention may further include, for any of I/O 249, 237, or 271, a video display unit (e.g., a liquid crystal display (LCD) or a cathode ray tube (CRT)). Computer systems or machines used to implement some or all of the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 245, 279, or 229 can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for determining carrier status of an autosomal recessive disease, the method comprising the steps of:

capturing, using molecular inversion probes, nucleic acid corresponding to a first locus that is linked to a second locus, wherein the second locus is diagnostic for an autosomal recessive disease;

sequencing said captured nucleic acid;

measuring a copy number of the first locus;

inferring a copy number of the second locus based on the copy number of the first locus; and determining disease status based upon the inferred copy number of the second locus.

2. The method of claim 1, wherein said autosomal recessive disease is spinal muscular atrophy.

3. The method of claim 2, wherein the first genomic locus is on intron 7 of an SMN1 or SMN2 gene or both.

4. The method of claim 3, wherein the second genomic locus is on exon 7 of an SMN1 gene.

5. The method of claim 4, wherein the first genomic locus is selected from rs212214 and rs212213.

6. The method of claim 1, wherein said sequencing step comprises a Sanger sequencing method or a next-generation sequencing method.

7. The method of claim 1, wherein said capturing step comprises isolating said nucleic acid from a sample comprising nucleic acid from a subject.

8. The method of claim 7, wherein said sample is a maternal blood sample.

9. The method of claim 8, wherein said maternal blood sample comprises cell free circulating nucleic acid.

10. The method of claim 9, wherein at least a portion of the cell free circulating nucleic acid is from a fetus being carried within the subject.

* * * * *